United States Patent [19]
Mohajer

[11] Patent Number: 5,279,307
[45] Date of Patent: Jan. 18, 1994

[54] COMBINATION EXO-ENDOCERVICAL SAMPLER

[76] Inventor: Reza S. Mohajer, 3115 W. Shore Dr., Orchard Lake, Mich. 48033

[21] Appl. No.: 962,701

[22] Filed: Oct. 19, 1992

[51] Int. Cl.⁵ ............................................. A61B 10/00
[52] U.S. Cl. .................................................. 128/757
[58] Field of Search .................... 128/749, 756-758

[56] References Cited

U.S. PATENT DOCUMENTS

| | | | |
|---|---|---|---|
| 3,774,590 | 11/1973 | McDonald | 128/2 B |
| 3,961,620 | 6/1976 | Schack et al. | 128/2 B |
| 4,054,127 | 10/1977 | Milan et al. | 128/2 B |
| 4,127,113 | 11/1978 | Nollan | 128/756 |
| 4,384,587 | 5/1983 | Milgrom | 128/757 |
| 4,620,548 | 11/1986 | Hasselbrack | 128/758 |
| 4,700,713 | 10/1987 | Kist | 128/756 |
| 4,754,764 | 7/1988 | Bayne | 128/756 |
| 4,759,376 | 7/1988 | Stormby | 128/756 |
| 4,762,133 | 8/1988 | Bayne et al. | 128/756 |
| 4,873,992 | 10/1989 | Bayne | 128/756 |
| 4,888,845 | 12/1989 | Ramm et al. | 15/182 |
| 5,022,408 | 6/1991 | Mohajer | 128/756 |

FOREIGN PATENT DOCUMENTS

| | | |
|---|---|---|
| 1429689 | 3/1976 | United Kingdom . |
| 2208603 | 12/1989 | United Kingdom . |
| 1016855 | 11/1991 | World Int. Prop. O. .......... 128/756 |

*Primary Examiner*—Max Hindenburg
*Attorney, Agent, or Firm*—Krass & Young

[57] ABSTRACT

A combination exo-endocervical sampler. The sampler includes an elongated handle portion having a free end and a non-linearly tapered row of flags disposed proximate the end opposite the free end. The flags are preferably configured to have a flat sampling surface and a convex opposed surface and are disposed at an acute angle with respect to the handle portion. A spatulate member is disposed on the handle portion proximate the row of flags at a point diametrically opposite thereto. A ledge extends along the handle member proximate its juncture with the spatulate member and serves to assist in the spreading of the separated exo- and endocervical samplers on to a two-tiered microscope slide. Optionally, a secondary row of flags is formed on an upper edge of the spatulate member to sweep the endocervix and transition zone when the device is rotated within the cervical canal.

10 Claims, 1 Drawing Sheet

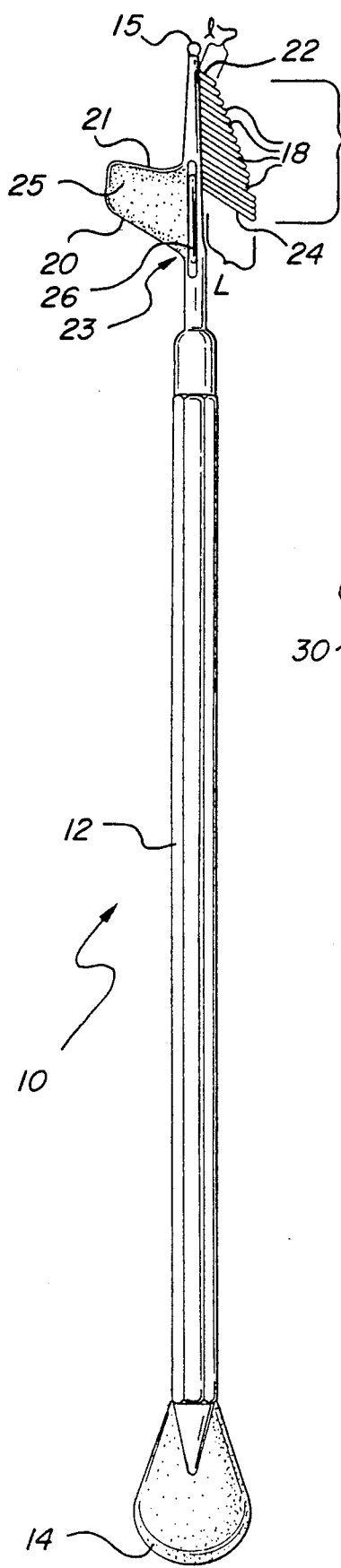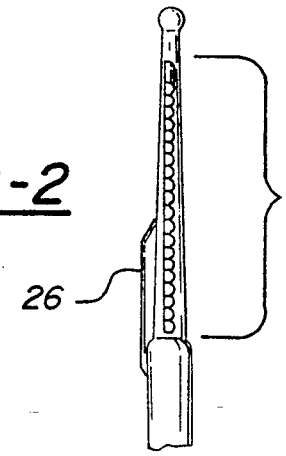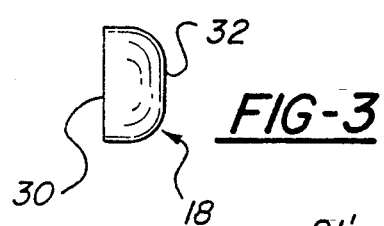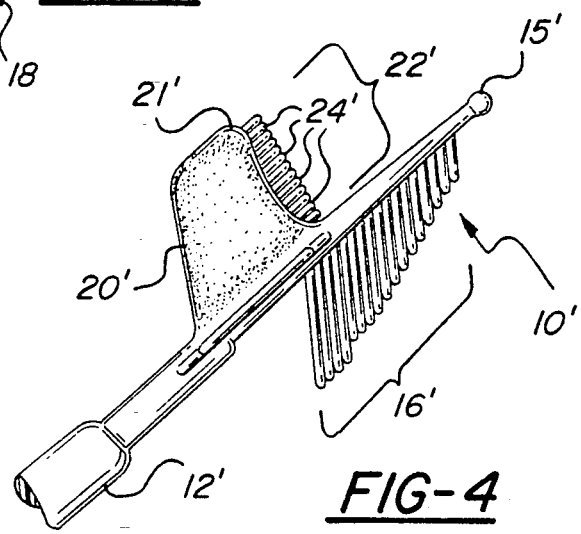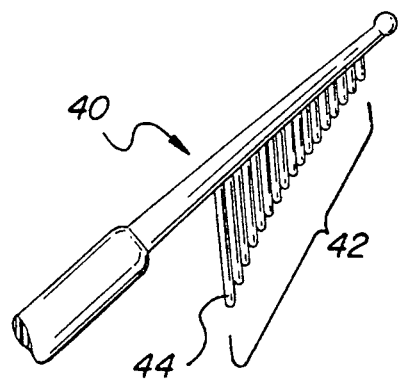

COMBINATION EXO-ENDOCERVICAL SAMPLER

BACKGROUND OF THE INVENTION

1. Field of the Invention

This invention relates to the field of collecting and preparing cervical smears for diagnostic purposes, and, more particularly, to an improved device for simultaneously collecting samples of both exocervical and endocervical cells.

2. Description of the Relevant Prior Art

U.S. Pat. No. 5,022,408, the disclosure of which is hereby incorporated by reference, describes in some detail the problems encountered with prior art cervical sampling devices. These problems include inadequacy of smear samples due to the absence of endocervical cells, excess mucous in the samples, failure to penetrate the depth of the endocervix, removal of immature cells from deeper layers of cervical tissue ("the brush effect"), abrasion of the endocervical wall which causes undesirable bleeding and obscure cervical samples, and the necessity of using two separate devices to obtain endo- and exocervical samples.

The '408 patent disclosed and claimed a combination exo-endocervical sampler. The sampler includes an elongated handle portion defining a longitudinal axis and having a free end. A row of flexible flags is disposed proximate the end of the handle portion opposite the free end. The flags are disposed at an acute angle with respect to the handle portion. A substantially longer, relatively rigid stop or filament is disposed on the handle portion proximate the row of flags. The filament serves as a stop when the device is inserted into the cervical os, and also scrapes the exocervical wall when the device is rotated 360 degrees. Rotation of the device also causes the row of flags to engage the surface of the endocervix. Therefore, when the device is removed from the cervical canal, two separated cell samples are obtained.

The sampler of the '408 patent is used to best advantage in preparing a cervical cell sample on a two-tiered microscope slide, such as that disclosed in FIG. 4 thereof. The sampler is simply wiped across the two-tier slide, thus depositing endocervical cells on the upper surface 46 thereof, and exocervical cells on the lower surface 48 thereof.

In clinical trials, the sampler of the '408 patent has shown a consistency in obtaining accurate cervical samples not attainable with the prior art. In a clinical trial involving over 300 samples obtained with the patented sampler, 99% accuracy was attained, with almost no false positive or false negative samples. Furthermore, the patented sampler does not cause bleeding, is relatively comfortable for the patient, is efficient and easy to use, and can be easily and cheaply manufactured by simple molding techniques.

However, clinical experience has shown that certain improvements to the basic patented device make it even easier and more efficient to use, particularly by medical personnel who do not have highly developed sampling skills. Thus, a need exists for an improved device which incorporates various features which improve the reliability of the sample obtained.

SUMMARY OF THE INVENTION

Disclosed and claimed herein is an improved combination exo-exocervical sampler. Like the device disclosed in the '408 patent, the sampler includes an elongated handle portion having a free end which is adapted to be grasped by the clinician. A row of flexible flags are disposed at the end of the handle portion opposite its free end and project therefrom at an acute angle. The flags are thin and flexible enough so that they may easily be inserted into the endocervical canal through the stenotic cervical os. An exocervical member in the form of a textured spatulate member is disposed at a location on the handle medial of said row of flags and proximate thereto, and diametrically opposed therefrom. The spatulate member has sufficient stiffness to act as a stop when the sampler is inserted into the vaginal canal of the patient. The purpose of the spatulate member is to sweep the exocervical wall as the device is rotated after it has been properly inserted.

The length of the flexible flags tapers from a shortest flag disposed proximate the opposite end of the handle portion to a longest flag disposed proximate the spatulate member. Preferably, the length of the successive flags increases according to a non-linear mathematical function; that is, the length of the flags does not increase in a simple linear progression, but increases geometrically so that the rate of increase in the lengths of the successive flags itself increases from shortest to longest. Because the rate of increase in the flag length is controlled by a non-linear algebraic function, the taper of the flags better conforms to the interior surface of the endocervix than was true in the prior art sampler.

Preferably, the handle portion is formed with a ledge disposed and aligned along the axis of the handle portion proximate the base of the spatulate member and extending therealong. The purpose of the ledge is to facilitate the spreading of the sample on the two-tiered microscope slide. The ledge abuts against the edge of the upper tier of the two-tier slide and guides the sampler as it is smeared along the slide.

In another preferred embodiment, the spatulate member tapers at its upper edge to define a thinner edge portion which serves to scrape cells from the exo- and transition portions of the cervical canal. Alternatively, a row of secondary flags can be disposed along the upper edge of the spatulate member. The secondary flags are disposed in a coplanar row along the upper edge and, generally, are of shorter length than the tapering, endocervical flags. The secondary flags serve to sweep the exo- and transition portions of the cervical canal as the sampler is rotated therein.

In yet another preferred embodiment, each of the plurality of tapering, endocervical flags has two opposed surfaces, a flat sampling surface and a convex rear surface.

BRIEF DESCRIPTION OF THE DRAWINGS

The following detailed description is best understood by reference to the following drawings, in which:

FIG. 1 is a perspective view of an improved exo-endocervical sampler according to the present invention;

FIG. 2 is a detail view of a portion of the cervical sampler of FIG. 1 rotated 90 degrees to better show the ledge formed thereon;

FIG. 3 shows a cross section of a typical flag of the sampler of FIG. 1;

FIG. 4 is an alternative embodiment of an exo-endocervical sampler according to the present invention; and FIG. 5 is yet another alternative embodiment of an exo-endocervical sampler according to the present invention.

DETAILED DESCRIPTION OF THE PREFERRED EMBODIMENTS

Throughout the following detailed description, like reference numerals are used to reference identical elements of the present invention shown in multiple figures thereof. Referring now to the drawing, and in particular to FIGS. 1 and 2, there is shown a cervical sampler 10 constructed according to the instant invention. The cervical sampler 10 comprises an elongated handle portion 12 having a free end 14. A row 16 of flexible, endocervical flags 18 are disposed on the end 15 of handle portion 12 opposite free end 14. As can be seen in FIG. 3, each of the flags 18 is configured to have two surfaces 30, 32. The sampling surface 30 is flat, whereas the rear surface 32 is at least partially convex. Due to their thinness, the flags 18 are relatively flexible and will not penetrate deeper layers of cervical tissue or cause bleeding or distortion of the cell samples when the cervical sampling is done. Furthermore, their flat sampling surface 30 provides a flat surface for obtaining an adequate sample. Moreover, since the flags 18 are disposed along handle portion 12 in a coplanar row 16, they project only from one side of handle portion 12. This reduces the diameter of the device and permits easier insertion thereof.

It is desirable that the flags 18 project from handle portion 12 at an acute angle therewith, as is shown in FIG. 1. In general, the flags will project from the handle 12 at an angle of approximately 45 degrees to 90 degrees, although still smaller angles may be employed. Furthermore, the flags 18 of row 16 are tapered in length such that the flag 22 having the shortest length l is closest to opposite end 15 and the flag 24 having the greatest length L is closest free end 14. Moreover, the rate of increase in the length of the flags 18 from shortest flag 22 to longest flag 24 itself increases. That is, the length of the flags 18 increases in a non-linear fashion. This means that the length l of longest flag 24 in relation to the length 1 of flag 22 is greater than it would be if the rate of increase were simply a linear function. The reason for the non-linear taper of the row 16 of flags 18 is that it has been found that such a non-linear taper more nearly conforms to the inner surface of the endocervix; thus, the flags 18 more effectively sweep cells from the endocervix than is the case for a sampler having flags with a linear taper.

Disposed on handle portion 12 proximate row 16 of flags 18 and medial thereof is a textured spatulate member 20. Because spatulate member 20 is relatively wide, it is stiff enough to serve as a stop when the device 10 is inserted into the cervical os of a patient. In the preferred embodiment shown in FIG. 1, the spatulate member 20 is disposed on handle portion 12 at a point approximately diametrically opposite the row 16 of flags 18. Spatulate member 20 is arranged in this manner with respect to row 16 to assist in engagement of the flags 18 with the endocervical surface when the device is in use. Preferably, spatulate member 20 is formed with a textured portion 25 on its surface. The texturing of the surface of spatulate member 20 serves to retain and hold a sample of exo- and transition cervical cells thereon.

Spatulate member 20 further comprises a top edge 21 and a base 23 defined by its juncture with handle portion 12. Preferably, the thickness of the spatulate member 20 decreases toward top edge 21, the better to scrape cells off of the exo and transition zone portions of the cervical canal. Furthermore, to assist in preparation of the cervical smear using a two-tiered microscope slide, such as is depicted in FIG. 4 of issued U.S. Pat. No. 5,022,408, a ledge 26, which is best seen in profile in FIG. 2 (a view of a portion of the cervical sampler 10 of FIG. 1 rotated 90 degrees, the spatulate member not being visible in this view) is formed on handle portion 12 proximate the base 23 of spatulate member 20.

An alternate embodiment 10' of the cervical sampler of the present invention is shown in FIG. 4. FIG. 4 merely depicts the elements of the sampler found proximate the free end 15' thereof, the remaining portions of the sampler 10' being similar to those of sampler 10 shown in FIG. 1. In the embodiment depicted in FIG. 4, a row 16' of coplanar flags is deposed proximate free end 15'. A spatulate member 20' is disposed on handle portion 12' in a manner similar to that described for the embodiment depicted in FIG. 1. Spatulate member 20' includes a top edge 21' having a row 22' of secondary flags 24' formed thereon. Generally, the secondary flags 24' are shorter than the lengths of the row 16' of main flags to be inserted into the endocervix. The shorter, secondary flags 24' serve to sweep the exocervix and transitional zone as the cervical sampler is rotated within the cervical canal.

FIG. 5 illustrates still another embodiment 40 of the present invention. In this embodiment, the spatulate member is eliminated, and the row of flags 42 is made somewhat longer than in the preceeding embodiments. The bottommost flag 44, and those proximate thereto are also longer than the bottommost flags in the preceeding embodiments and these flags function to sample the exocervix and transition zone.

Preferably, the cervical sampler of the present invention is unitary in construction. This unitary construction results in ease of manufacture, as well as lower cost, a critical factor for a device commonly used in mass screening. The device may be molded in any of a number of synthetic polymeric resins, such as polyethylene, polypropylene, polyester, nylon, polystyrene, polyvinylacetate, or a block copolymer of a polybutylene terepthalate polyester and a long chain polyetherglycol. One such commercially available material is a block copolymer consisting of a higher (crystalline) segment of polybutylene terepthalate and a soft (amorphous) segment based on a long chain polyetherglycol. Such materials are sold by the Dupont Corporation under the tradename Hytrel. Hytrel polymers are available in FDA-approved food grades.

While the present invention has been described with reference to certain embodiments and exemplifications thereof, the scope of the invention is not limited to those embodiments and exemplification. For example, the number of flags may differ from those shown. Also, the secondary flags may differ in number and length from those depicted. Furthermore, the spatulate member may be configured somewhat differently from that depicted. Doubtless other variations may occur to one skilled in the art without departing from the teachings of the present invention. The present invention is not limited solely to the exemplifications and embodiments depicted herein, but solely by the claims appended hereto and reasonable equivalents thereof.

I claim:

1. A combination exo-endocervical sampler comprising:

an elongated handle portion defining a longitudinal axis; and a plurality of flexible flags disposed in a coplanar row proximate an end of said handle portion, said flags projecting from said handle portion at an acute angle with respect thereto for insertion into the endocervical canal, the lengths of said plurality of flags successively increasing according to a non-linear function wherein the rate of increase in the lengths of the flags changes from shortest flag proximate said free end to a longest flag.

2. The sampler of claim 1, further including a spatulate member projecting from said handle at a location thereon proximate said longest flag, and medial thereof and diametrically opposed thereto, said spatulate member serving as a stop when the sampler is inserted into the endocervical canal.

3. The sampler of claim 2 wherein said spatulate member tapers at an upper edge thereof to define a thin edge portion, said edge portion serving to scrap cells from the exo and transition portions of the cervical canal.

4. The sampler of claim 2 wherein the spatulate member further comprises a row of secondary flags disposed on an upper edge thereof in a mutually coplanar row to sweep the exo- and transition portions of the cervical canal.

5. The sampler of claim 2 wherein said spatulate member includes a textured surface portion formed thereon.

6. The sampler of claim 1 further comprising a raised ledge formed on said handle member proximate said longest flag and extending along a portion of the longitudinal axis of the handle member coextensive with said spatulate member.

7. The sampler of claim 1 wherein each of said plurality of flags has opposed surfaces including at least a first flat surface and a second convex surface.

8. A combination exo-endocervical sampler comprising:

an elongated handle portion defining a longitudinal axis;

a plurality of flexible flags disposed in a mutually coplanar row proximate one end of said handle portion and projecting therefrom at an acute angle for insertion into the endocervical canal;

an exocervical spatulate member disposed at a location on said handle portion medial of said row of flags, said spatulate member including a base defined by the juncture of the spatulate member with the handle member, said spatulate member serving as a stop when the sampler is inserted into the endocervical canal; and a ledge formed on said handle member proximate said base of said spatulate member and extending along a portion of the longitudinal axis of the handle member coextensive with said spatulate member to assist in the spreading of a sampler of cervical fluid obtained with said sampler onto a slide.

9. A combination exo-endocervical sampler comprising:

an elongated handle portion defining a longitudinal axis;

a plurality of flexible flags disposed in a mutually coplanar row proximate one end of said handle portion and projecting therefrom at an acute angle with respect thereto for insertion into the endocervical canal;

a spatulate member projecting from said handle at a location medial of said plurality of flags and diametrically opposite thereto, said spatulate member including an upper edge and a base defined by the juncture of the spatulate member with the handle member, said sampler further comprising a raised ledge formed on said handle member proximate said base of said spatulate member and extending along a portion of the longitudinal axis of the handle member coextensive with said spatulate member; and a row of secondary flags disposed on said upper edge of said spatulate member in a mutually coplanar row to sweep the exo and transition portions of the cervical canal.

10. The sampler of claim 9 wherein said spatulate member includes a textured surface portion formed thereon.

* * * * *